US008241276B2

(12) United States Patent
Epstein et al.

(10) Patent No.: US 8,241,276 B2
(45) Date of Patent: Aug. 14, 2012

(54) RF ABLATION DEVICE WITH JAM-PREVENTING ELECTRICAL COUPLING MEMBER

(75) Inventors: Gordon Epstein, Pleasanton, CA (US);
Bruce Lee, Pleasanton, CA (US);
Jeffrey M. Cohen, Pleasanton, CA (US);
Adam Hagmann, Pleasanton, CA (US);
Richard Spero, Brentwood, CA (US)

(73) Assignee: Halt Medical Inc., Pleasanton, CA (US)

( * ) Notice: Subject to any disclaimer, the term of this patent is extended or adjusted under 35 U.S.C. 154(b) by 856 days.

(21) Appl. No.: 11/940,289

(22) Filed: Nov. 14, 2007

(65) Prior Publication Data
US 2009/0187182 A1    Jul. 23, 2009

(51) Int. Cl.
*A61B 18/14*    (2006.01)
(52) U.S. Cl. ........................................... 606/41
(58) Field of Classification Search ............. 606/41
See application file for complete search history.

(56) References Cited

U.S. PATENT DOCUMENTS

| 35,330 | A | 5/1862 | Silvester |
| 3,991,770 | A | 11/1976 | LeVeen |
| 4,016,886 | A | 4/1977 | Doss et al. |
| 4,074,718 | A | 2/1978 | Morrison, Jr. |
| 4,080,959 | A | 3/1978 | Leveen |
| 4,095,602 | A | 6/1978 | Leveen |
| 4,119,102 | A | 10/1978 | LeVeen |
| 4,140,130 | A | 2/1979 | Storm, III |
| 4,154,246 | A | 5/1979 | LeVeen |

(Continued)

FOREIGN PATENT DOCUMENTS
DE    2124684 A1    11/1972

OTHER PUBLICATIONS

Bergamini, MD, et al., Laparoscopic radiofrequency thermal ablation: A new approach to symptomatic uterine myomas, American Journal of Obsterics and Gynecology (2005) 192, 768-73, Varese, Italy.

*Primary Examiner* — Michael Peffley
*Assistant Examiner* — Daniel Fowler
(74) *Attorney, Agent, or Firm* — Handal & Morofsky LLC (57) ABSTRACT

The inventive ablation element comprises an elongated cannula having a proximal end and a distal end. The cannula defines an internal lumen within the cannula and a cannula axis. A plurality of conductors contained within the lumen, each of the conductors has a proximal end proximate the proximal end of the cannula, and a distal end proximate the distal end of the cannula. A plurality of ablation stylets each has a proximal end and a distal end, and each coupled at the respective proximal end of the stylet to the distal end of a respective conductor, the stylets comprise a deflectable material, the conductors together with their respective stylets being mounted for axial movement. A trocar point defined proximate the distal end of the cannula. A deflection surface positioned between the trocar point and the proximal end of the cannula, the deflection surface being configured and positioned to deflect, in response to axial movement of the stylets in a direction from the proximate end of the cannula to the distal end of the cannula, at least some of the stylets laterally with respect to the cannula axis in different directions along substantially straight paths, the paths defining an ablation volume.

8 Claims, 9 Drawing Sheets

U.S. PATENT DOCUMENTS

| | | |
|---|---|---|
| 4,230,129 A | 10/1980 | LeVeen |
| 4,285,346 A | 8/1981 | Armitage |
| 4,290,435 A | 9/1981 | Waggott |
| 4,303,636 A | 12/1981 | Gordon |
| 4,346,715 A | 8/1982 | Gammell |
| 4,375,220 A | 3/1983 | Matvias |
| 4,545,368 A | 10/1985 | Rand et al. |
| 4,565,200 A | 1/1986 | Cosman |
| 4,676,258 A | 6/1987 | Inokuchi et al. |
| 4,709,701 A | 12/1987 | Weber |
| 4,773,864 A | 9/1988 | Holt |
| 4,823,791 A | 4/1989 | D'Amelio et al. |
| 4,881,543 A | 11/1989 | Trembly et al. |
| 4,887,614 A | 12/1989 | Shirakami et al. |
| 4,955,884 A | 9/1990 | Grossi et al. |
| 4,962,761 A | 10/1990 | Golden |
| 5,003,991 A | 4/1991 | Takayama et al. |
| 5,007,908 A | 4/1991 | Rydell |
| 5,010,897 A | 4/1991 | LeVeen |
| 5,099,756 A | 3/1992 | Franconi et al. |
| 5,151,101 A | 9/1992 | Grossi et al. |
| 5,190,517 A | 3/1993 | Zieve et al. |
| 5,190,541 A | 3/1993 | Abele et al. |
| 5,234,004 A | 8/1993 | Hascoet et al. |
| 5,257,451 A | 11/1993 | Edwards et al. |
| 5,273,535 A | 12/1993 | Edwards et al. |
| 5,275,162 A | 1/1994 | Edwards et al. |
| 5,282,797 A | 2/1994 | Chess |
| 5,293,863 A | 3/1994 | Zhu et al. |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,322,503 A | 6/1994 | Desai |
| 5,328,467 A | 7/1994 | Edwards et al. |
| 5,334,193 A | 8/1994 | Nardella |
| 5,342,357 A | 8/1994 | Nardella |
| 5,348,554 A | 9/1994 | Imran et al. |
| 5,363,861 A | 11/1994 | Edwards et al. |
| 5,366,490 A | 11/1994 | Edwards et al. |
| 5,368,592 A | 11/1994 | Stern et al. |
| 5,370,678 A | 12/1994 | Edwards et al. |
| 5,383,917 A | 1/1995 | Desai et al. |
| 5,385,544 A | 1/1995 | Edwards et al. |
| 5,398,683 A | 3/1995 | Edwards et al. |
| 5,403,311 A | 4/1995 | Abele et al. |
| 5,409,453 A | 4/1995 | Lundquist et al. |
| 5,423,807 A | 6/1995 | Milder |
| 5,423,808 A | 6/1995 | Edwards et al. |
| 5,423,811 A | 6/1995 | Imran et al. |
| 5,433,708 A | 7/1995 | Nichols et al. |
| 5,435,805 A | 7/1995 | Edwards et al. |
| 5,437,662 A | 8/1995 | Nardella |
| 5,456,662 A | 10/1995 | Edwards et al. |
| 5,458,596 A | 10/1995 | Lax et al. |
| 5,458,597 A | 10/1995 | Edwards et al. |
| 5,462,521 A | 10/1995 | Brucker et al. |
| 5,470,308 A | 11/1995 | Edwards et al. |
| 5,470,309 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,531,677 A | 7/1996 | Lundquist et al. |
| 5,536,267 A | 7/1996 | Edwards et al. |
| 5,540,655 A | 7/1996 | Edwards et al. |
| 5,542,915 A | 8/1996 | Edwards et al. |
| 5,542,916 A | 8/1996 | Hirsch et al. |
| 5,542,928 A | 8/1996 | Evans et al. |
| 5,545,161 A | 8/1996 | Imran |
| 5,545,171 A | 8/1996 | Sharkey et al. |
| 5,545,193 A | 8/1996 | Fleischman et al. |
| 5,546,267 A | 8/1996 | Frederiksen et al. |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,560,358 A | 10/1996 | Arnold et al. |
| 5,562,703 A | 10/1996 | Desai |
| 5,582,610 A | 12/1996 | Grossi et al. |
| 5,662,680 A | 9/1997 | Desai |
| 5,672,173 A | 9/1997 | Gough et al. |
| 5,672,174 A | 9/1997 | Gough et al. |
| 5,683,384 A | 11/1997 | Gough et al. |
| 5,728,143 A | 3/1998 | Gough et al. |
| 5,759,162 A | 6/1998 | Oppelt et al. |
| 5,782,827 A | 7/1998 | Gough et al. |
| 5,810,809 A * | 9/1998 | Rydell ........................... 606/49 |
| 5,911,036 A | 6/1999 | Wright et al. |
| 5,935,123 A | 8/1999 | Edwards et al. |
| 5,979,453 A | 11/1999 | Savage et al. |
| 6,002,968 A | 12/1999 | Edwards |
| 6,036,689 A | 3/2000 | Tu et al. |
| 6,066,139 A | 5/2000 | Ryan et al. |
| 6,071,280 A | 6/2000 | Edwards et al. |
| 6,190,383 B1 | 2/2001 | Schmaltz et al. |
| 6,212,433 B1 | 4/2001 | Behl |
| 6,217,518 B1 | 4/2001 | Holdaway et al. |
| 6,254,601 B1 | 7/2001 | Burbank et al. |
| 6,355,033 B1 | 3/2002 | Moorman et al. |
| 6,468,273 B1 | 10/2002 | Leveen et al. |
| 6,575,967 B1 | 6/2003 | Leveen et al. |
| 6,575,969 B1 | 6/2003 | Rittman, III et al. |
| 6,638,275 B1 * | 10/2003 | McGaffigan et al. ........... 606/41 |
| 6,837,887 B2 | 1/2005 | Woloszko et al. |
| 6,840,935 B2 | 1/2005 | Lee |
| 2002/0133150 A1 | 9/2002 | Whayne et al. |
| 2002/0161385 A1* | 10/2002 | Wiener et al. .................. 606/169 |
| 2002/0183740 A1* | 12/2002 | Edwards et al. ................. 606/41 |
| 2003/0125729 A1 | 7/2003 | Hooven et al. |
| 2003/0130711 A1 | 7/2003 | Pearson et al. |
| 2003/0199868 A1 | 10/2003 | Desai et al. |
| 2004/0215182 A1 | 10/2004 | Lee |
| 2004/0254572 A1 | 12/2004 | McIntyre et al. |
| 2005/0085838 A1* | 4/2005 | Thompson et al. ........... 606/170 |
| 2005/0149013 A1 | 7/2005 | Lee |
| 2005/0240174 A1* | 10/2005 | Pearson et al. .................. 606/41 |
| 2006/0079879 A1* | 4/2006 | Faller et al. ..................... 606/40 |
| 2006/0079880 A1* | 4/2006 | Sage et al. ....................... 606/41 |
| 2006/0149226 A1* | 7/2006 | McCullagh et al. ............ 606/41 |
| 2006/0189972 A1 | 8/2006 | Grossman |
| 2006/0195126 A1* | 8/2006 | Snow et al. .................... 606/159 |
| 2006/0217702 A1* | 9/2006 | Young ............................ 606/41 |
| 2006/0241577 A1* | 10/2006 | Balbierz et al. ................. 606/32 |
| 2006/0247620 A1* | 11/2006 | Bourne et al. ................... 606/41 |
| 2006/0271036 A1* | 11/2006 | Garabedian et al. ............ 606/41 |
| 2007/0006215 A1 | 1/2007 | Epstein et al. |
| 2007/0016183 A1 | 1/2007 | Lee et al. |

* cited by examiner

RF ABLATION DEVICE WITH JAM-PREVENTING ELECTRICAL COUPLING MEMBER

CROSS REFERENCE TO RELATED APPLICATION

Not Applicable

BACKGROUND

In the United States, approximately 230,000 women have hysterectomies annually. The primary reason for performing a hysterectomy is the presence of uterine fibroids. These fibroids grow in the wall of the uterus and may range in size up to several inches across. In the United States alone, there are more than six million women with uterine fibroid symptoms who prefer to suffer, rather than endure the risks and inconveniences associated with major surgery, especially a major surgery that results in infertility. Outside of the United States, the situation is much the same, with millions of women suffering with fibroids in need of a safe alternative to hysterectomy.

Recently, another treatment option (uterine artery embolization) has been introduced. Generally, this procedure involves embolization of the arteries which feed the urine fibroid. This results in cutting off the blood supply to the fibroid and the shrinkage of the fibroid over time. However, the unacceptably high rate of complications severely limits its appeal to patients.

Myomectomy, generally involves the surgical removal of the fibroid through the use of classical surgical procedures, and is another treatment option. However, due to its high rate of complications and long recovery time, this option is also not very appealing to patients. Typical complications involve risk of infection, relatively severe post-surgical pain, damage to the uterus and other risks normally associated with such types of surgery. Moreover, such damage may be relatively subtle and may only come to light when the uterus begins to swell in pregnancy and ruptures at a weak point created during the surgery, resulting in loss of the fetus.

Still another alternative to treat the discomfort associated with uterine fibroids is the removal of the endometrium which lines the uterus. However, this procedure results in infertility.

In an attempt to address these issues, an RF ablation probe of the type used to treat tumors in the human liver by hyperthermia has been successfully demonstrated to substantially shrink or eliminate uterine fibroids.

See, for example, U.S. Pat. No. 6,840,935 issued to Lee on Jan. 11, 2005, the disclosure of which is incorporated herein by reference. In that patent a method for treating pelvic tumors, such as uterine leiomyomata, includes inserting an ablation apparatus into a pelvic region and positioning the ablation apparatus either proximate to or into a pelvic tumor. The method further includes using a laparoscope and an imaging device, such as an ultrasound machine, to confirm the location of the pelvic tumor and placement of the ablation apparatus. An ablation apparatus with multiple needles or deployable arms that are inserted into the pelvic tumor is disclosed. The method involves delivering electromagnetic energy or other energy through the ablation apparatus to the pelvic tumor to induce hyperthermia and ablate the tumor.

The particular device disclosed for ablating the tumor in U.S. Pat. No. 6,840,935 is of the type disclosed in U.S. Pat. No. 5,728,143, issued to Gough et al. on Mar. 17, 1998. Generally, that device comprises a plurality of resilient springy RF ablation antennae, or stylets, which are preformed with a curved configuration which they assume after exiting a sharp trocar-tipped catheter. The tip of the catheter is deployed in uterine fibroid tissue to be destroyed. The stylets are then deployed into the tissue to be destroyed. Generally, as the antennae exit the trocar tip, they pierce the tissue of the uterine fibroid along curved paths which are defined by the preformed springy shape of the stylet. The deployed stylets with their respective preformed shapes and the positions within which they are deployed thus define the ablation volume. Various shape volumes may be defined by varying the configuration of the curves which are preformed into the different springy stylets convey given trocar-pointed catheter. Such devices are manufactured by Rita Medical Systems of Mountain View, Calif. The hallmark of such devices is that the stylets assume their pre-formed configuration as they emerge from the trocar tip.

Another approach is illustrated by copending U.S. patent application Ser. No. 11/173,928, entitled Radio Frequency Ablation Device for the Destruction of Tissue Masses filed on Jul. 1, 2005, the disclosure of which is incorporated by reference and copending U.S. patent application Ser. No. 11/429,921, entitled Anchored RF Ablation Device for the Destruction of Tissue Masses filed on May 8, 2006, the disclosure of which is incorporated by reference. The devices in both of these applications have in common the feature of deflecting the stylet and causing it to follow a path which is substantially straight (or at least straighter path than that in the Rita Medical device) as it advances through tissue to be ablated.

SUMMARY OF THE INVENTION

In accordance with the invention an ablation element comprises an elongated cannula having a proximal end and a distal end. The cannula defines an internal lumen within the cannula and a cannula axis. A trocar point is positioned proximate the distal end of the cannula. A conductor is contained within the cannula. The conductor has a proximal end and a distal end. The distal end of the conductor is proximate the distal end of the cannula. A plurality of ablation stylets each has a proximal end and a distal end, and each is coupled at the respective proximal end of the stylet to the distal end of the conductor. The stylets comprise a deflectable material and define a substantially straight shape. The conductor together with the stylets are mounted for axial movement within the cannula.

The inventive structure allows movement of a stylet assembly, for example comprising a plurality of stylets driven by a relatively rigid motor member together with a wire bundle associated, for example, with a plurality of temperature sensing elements. This allows the wire bundle to remain in a linear configuration during movement of the stylet assembly, and substantially maintains the distance between the end of the wire bundle and the stylet assembly. The same is achieved by simultaneously driving the motor member and the end of the wire bundle, for example an end mounted on a support member, with a folded flexible printed circuit ribbon whose folded length varies as said motor member is moved in order to accommodate the varying distance between a stationary end of the printer circuit ribbon and the stylet assembly.

Thus, the thermocouple wires are not loosely bundled and are not free to move within a slidable operator which typically moves up and down the length of the handle to advance the tube upon which the stylists are supported and by which the stylets are advanced. In contrast, in the present invention, the thermocouple wires are secured to a first set of contacts on a fixed end of a flexible printed circuit member which is mounted axially to the ablation stylet support tube. The thermocouple wires extend forward toward the ablation end of the instrument. The flexible printed circuit member extends backwards to an interface with a cable linking the instrument to the console, thus providing the output of the thermocouple wires to a console which controls ablation energy. The flexible printed circuit also includes a contact for providing RF energy to the ablation stylets. A third set of contacts associated with the flexible circuit bring the system in contact with the buttons which control navigation of functions on the console. Selective actuation of these buttons causes, for example, the sequential display of screens on the console display with various functional alternatives presented, as well as navigation between selection of such functional alternatives, as may be desired by the surgeon. Thus the buttons are brought into contact with appropriate connectors in the cable connecting the console to the probe.

A deflection surface is positioned between the tip of the trocar point and the proximal end of the cannula. The deflection surface is configured and positioned to deflect, in response to axial movement of the stylets in a direction from the proximal end of the cannula to the distal end of the cannula, at least one of the stylets laterally with respect to the cannula axis in different directions along paths which are substantially straight for that portion of the stylet which has exited the trocar point. These paths define an ablation volume.

The conductor may be selected from the group consisting of electrical conductors, radio frequency conductors, microwave conductors and optical conductors or light pipes.

Each of the stylets may be configured to assume a substantially straight configuration in the absence of external forces.

An ablation element further comprises a motor member (for example one driven by the finger of the surgeon performing the ablation procedure) or members coupled to the conductors to drive axial movement of the stylets in directions from the proximal end of the cannula to the distal end of the cannula, and from the distal end of the cannula to the proximal end of the cannula through a plurality of positions. The trocar point may be defined at the distal end of a trocar member, the trocar member having an outside surface, the cannula having an outside surface, the trocar member having a proximal end secured proximate to the distal end of the elongated cannula, and the outside surface of the cannula and the outside surface of the trocar point defining a trocar surface. The trocar member acts as a stylet mandrel to deflect the stylets, which may be electrodes, along paths which are substantially straight after the stylets exit the mandrel into the tissue to be ablated.

The deflection surface comprises a number of ramps defined proximate the proximal end of the trocar point, the distal ends of the stylets being positionable proximate to the ramps and within the trocar surface.

The conductor and the stylets are electrical conductors, and each of the stylets may be configured to assume a substantially straight configuration in the absence of external forces.

The deflection surface comprises a plurality of channels guiding the distal ends of the stylets to the ramps. The cannula may be secured to the trocar member with the outside surface of the cannula proximate to the outside surface of the trocar member.

The ablation element also comprises an anchor mounted for movement between an internal position disposed within the trocar surface and an anchoring position extending laterally from the trocar surface through points external of the lumen; and a drive member disposed within the lumen and coupled to the anchor to drive the anchor between the internal position and the anchoring position.

The anchor comprises at least two pointed members mounted for movement in directions which have vector components which extend away from the axis of the cannula and away from each other. The pointed members also preferably extend in a direction with a vector component that extends in a direction opposite to the direction in which the trocar point extends.

The conductors are driven by a drive mechanism which allows the conductors to move independently. The conductors have a length, a width and a thickness, the width being greater than the thickness, and terminate in a point oriented to allow deflection by the deflection surface. The conductors extend in different directions when they exit the deflection surface and extend to a variable extent. The conductors are driven by a drive circuit which varies the amount of energy supplied to the stylets and/or the length of the stylets and/or the length of the time during which power is supplied to the stylets and/or the angular orientation of the ablation element (through the variation of ramp deflection angle.

The parameters of stylet length, stylet power, stylet actuation time and/or angular orientation may be controlled by a computer in response to a computer program having an input comprising feedback information from the tissue area being operated on and/or a preset program.

The anchor is mounted for movement between an internal position disposed within the trocar surface and an anchoring position extending laterally from the trocar surface through points external of the lumen. The drive member may be disposed within the lumen and coupled to the anchor to drive the anchor between the internal position and the anchoring position. The desired motive force for advancing the stylets and/or optional anchors may be provided by a finger operated slidably mounted gripping surface which the surgeon uses to manually advance the conductor and the stylets attached to the end of the conductor. The gripping surface may be slidably mounted on a handle within which the proximal end of the trocar is mounted. The anchor comprises at least two pointed members mounted for movement in directions which have vector components which extend away from the axis or the cannula and away from each other.

As alluded to above, the front end of the inventive catheter is a trocar point defined at the distal end of a trocar member. The trocar member has an outside surface. The cannula has an outside surface, and the trocar member has a proximal end secured proximate to the distal end of the elongated cannula. The outside surface of the cannula and the outside surface of the trocar point define the trocar surface. The trocar member bears a plurality of deflection surfaces. The deflection surface comprises a number of ramps defined within the trocar member. The distal ends of the stylets are positionable proximate to the deflection surfaces and within the trocar surface.

In accordance with a particularly preferred embodiment of the invention, it is contemplated that a graphical user interface and a pair of electrical switches, for example a joystick and a pushbutton, will be used to switch between operating parameter options for the inventive catheter which are displayed on a graphical user interface (or other information conveying device such as an audio cue generator). The surgeon navigates a menu, for example, using a joystick looking at or hearing an electronically generated audio signal, such as a voice, presenting various options and selects the desired option by pushing the electrical switch. In principle, this can be done on a single switch incorporating joystick and pushbutton features.

Optionally, the electrical switches which operate the system may be recessed partially or fully in order to minimize the likelihood of unintentional actuation. Additional protection may be provided by requiring two motions within a relatively short period of time in order to achieve a change in the control of the system.

In accordance with a particularly preferred version of the invention, this is achieved by having a human voice present options and acknowledge instructions, which may be given to the system orally using voice recognition technology. This allows the surgeon to operate without having to look away from visual displays guiding the operation, the patient, instruments and so forth, thus removing potential losses of information. A display simultaneously displays all relevant information to provide a quicker provision of information to the surgeon.

In accordance with the invention it is contemplated that laser manufacturing techniques may be used to manufacture the anchors and perhaps the anchor deflection surfaces.

Preferably, the point of the trocar is milled to a point with three surfaces. Stylets are milled in the manner of a hypodermic needle. Stylets are oriented to cooperate with the deflection surfaces which deflect them. A cooperating low friction insulator ring, for example, made of Teflon, cooperates with the deflection surfaces to deflect hypotube electrode stylets.

The present invention contemplates the use of rearwardly deployed anchoring stylets which act as retractable barbs for maintaining the position of the trocar point during forward deployment of the radiofrequency (RF) electrode ablation stylets.

In accordance with the present invention, a stylet operating member, optionally a stylet push member, which may be a tube, is positioned on one side of a tubular compression/tension operator, for example on the inside of the compression/tension operator, Similarly, in accordance with the present invention, and anchor member operating member, optionally an anchor pull member, which may be a tube, is positioned on the other side of a tubular compression/tension operator, for example on the outside of the compression/tension operator. Such outside placement is particularly advantageous in the case where the anchoring member is of relatively wide dimension and large size.

In accordance with a preferred embodiment of the invention, the compression tension operator is secured at the proximal end to the handle of the ablation instrument and at the distal end to the anchoring member deflection surface and the hypotube electrode stylet deflection surface.

The invention contemplates a plurality of hypotube electrode stylets which are bound together as a unitary structure and advanced by a single push tube or wire.

It is also contemplated that the inventive instrument will include channels for flushing clean. In accordance with the inventive system, the frequency with which flushing should be performed is minimized through the use of a trocar front face which is substantially closed (except for a single undetected hypotube which exits the front face of the trocar) and providing for exit of hypotubes through the cylindrical side wall of the trocar point.

In accordance with a particularly preferred embodiment of the invention, the anchor member is separate from the anchor push tube, and is connected it to by mating or other interlocking structure.

Deflection surfaces for both the hypotube stylets and anchors are selected to result in strains in the range of 2% to 8%, preferably about 4%, for example 3.5% to 4.5%, which represents a reasonable compromise between instrument longevity and a relatively large amount of deflection.

An insulation sleeve is positioned between the anchors and the hypotube stylets in order to allow separate electrical actuation and ablation with either or both of the anchors and the hypotube stylets.

The hypotube stylets contain thermocouples which are used to measure the temperature of ablated tissue, thus ensuring that the tissue will be raised to the correct temperature for a sufficient period of time to ablate tissue resulting in the creation of necrotic tissue which may be absorbed by the body.

In accordance with the preferred embodiment of the invention, hypotube stylets are deployed forwardly or distally while anchors are deployed in a proximal direction or rearwardly. Alternatively, the hypotube stylets may be deployed in a proximal direction or rearwardly, while anchors are deployed forwardly or distally.

As compared to a conventional hysterectomy, the present invention is directed to a device for the treatment of uterine fibroids and other tissue masses that meets the needs of women by conserving the uterus and reducing recovery time from 6-8 weeks to 3-10 days.

In accordance with the invention, it is contemplated that the inventive stylet driving mechanism may be used in conjunction with a wide variety of stylets and stylet assemblies to allow movement thereof while providing for electrical coupling. A device in which the inventive stylet coupling of member may be used is illustrated in United States patent publication number 2070006215 A1, the disclosure of which is incorporated herein by reference.

DETAILED DESCRIPTION OF THE BEST MODE

Figure 1:
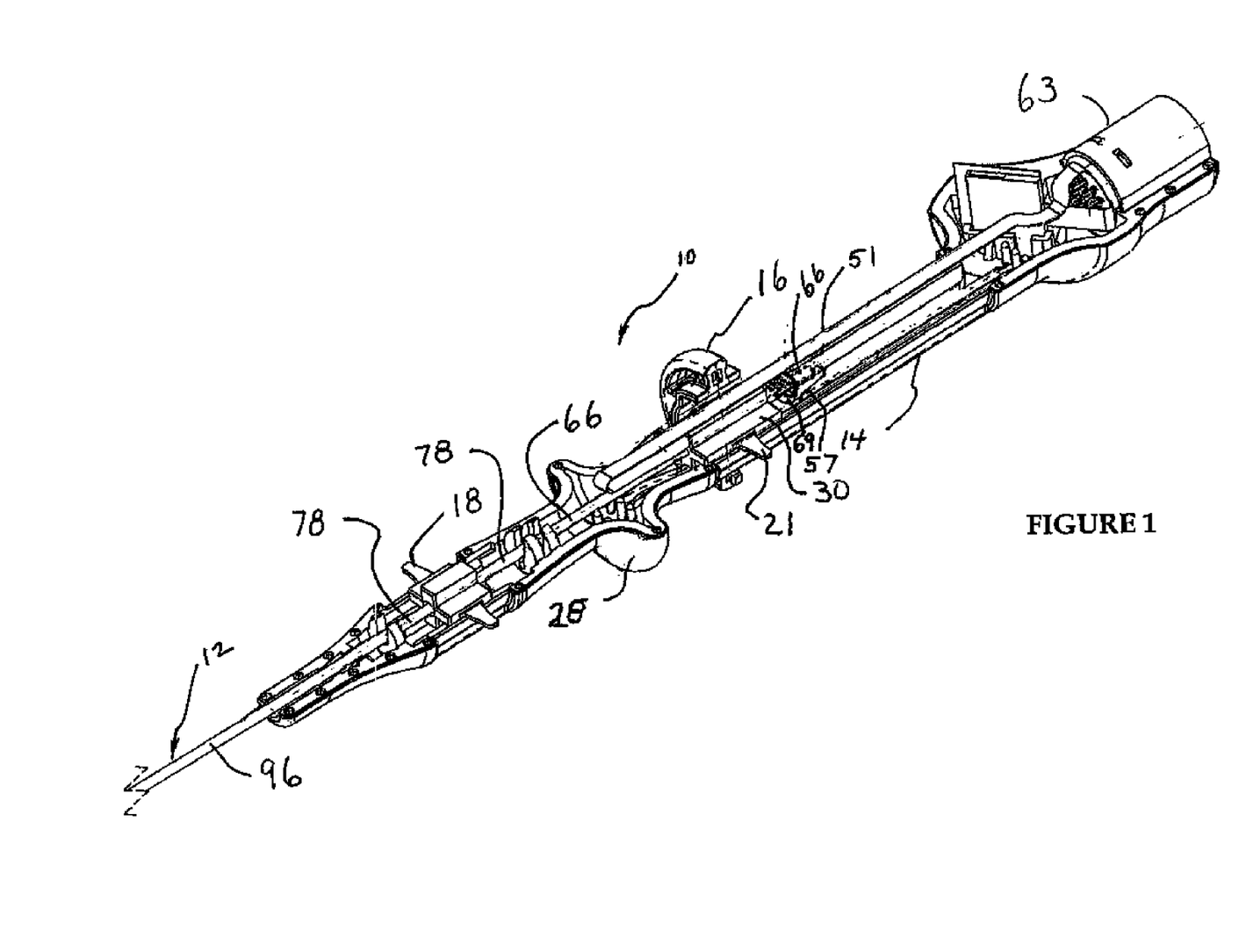
FIG. 1 is a perspective view of the multiple antenna ablation device of the invention with one of two housing halves removed to illustrate its operation.

Referring to FIG. 1, an ablation instrument 10 constructed in accordance with the present invention is illustrated. Instrument 10 comprises a catheter portion 12 and a handle portion 14. Ablation instrument 10 is illustrated with one of the two mating handle halves 28 removed, in order to reveal its internal parts and workings in connection with the following description.

Figures 2, 3:
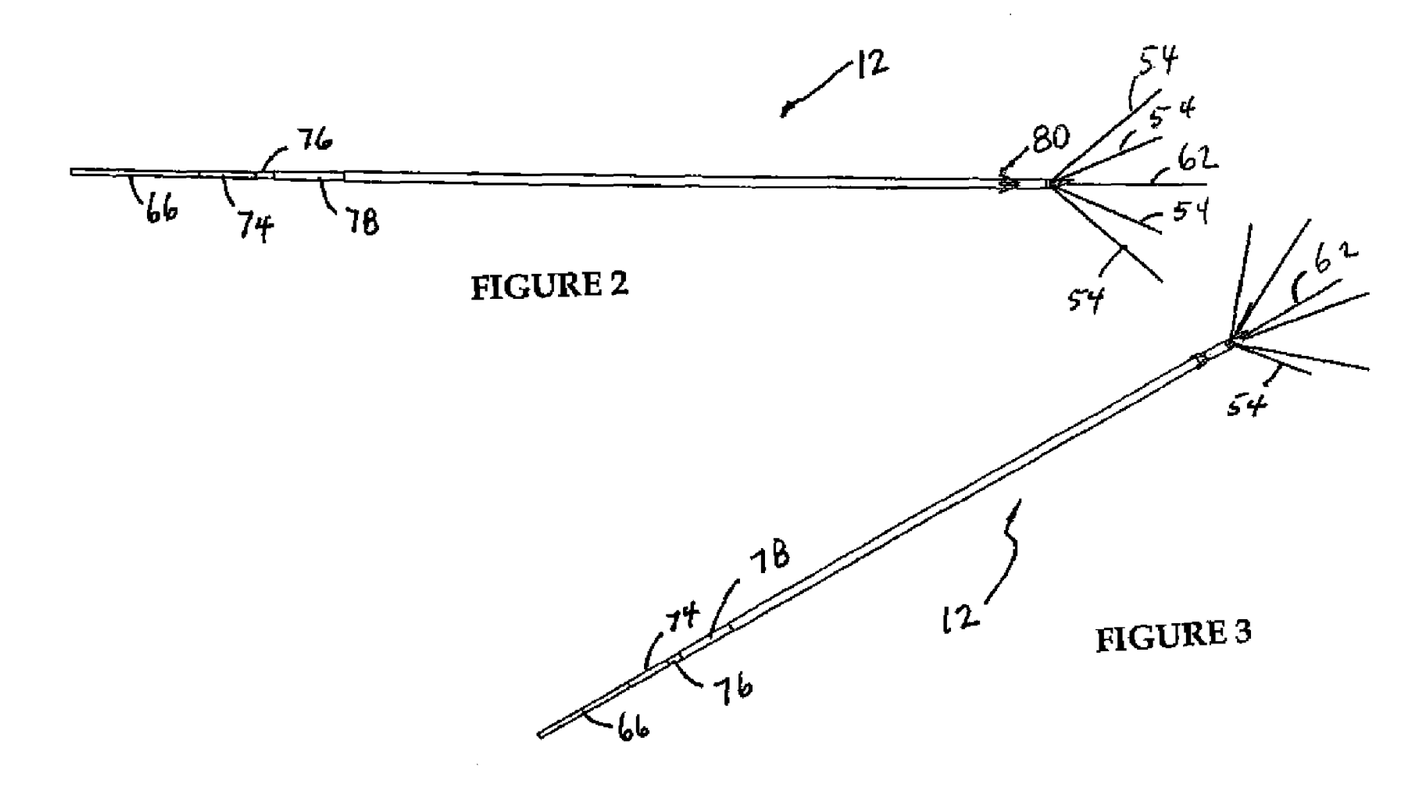
FIG. 2 is a plan view of the catheter with seven hypotube ablation electrodes and four anchors deployed.
FIG. 3 is a perspective view of the catheter structure of FIG. 2.

Referring to FIGS. 1, 2 and 3, the inventive ablation instrument 10 is illustrated in the fully forward ablation position, which the instrument takes after full advancement of stylets 54 into tissue, for example, tissue to be subjected to ablation by being treated with radiofrequency energy. In this position, the trocar 32 with its point 34 provide catheter 12 with a simple thin smooth pointed surface well-suited to penetrate healthy tissue while doing minimal damage. At the same time, the sharpness of the point and the relatively stiff, though somewhat flexible, nature of catheter 12 enables accurate steering of the point and control of the path of penetration. In the case of the treatment of uterine fibroids, such steering is achieved largely by manipulation of the uterus coupled with advancement of the catheter 12.

It is noted that while the invention is illustrated in the context of an ablation device incorporating a trocar point, the invention may be applied to ablation instruments with rounded tips, such as those used to enter the body through naturally existing physiological paths, such as urethra, and so forth.

Handle portion 14 includes a pair of actuators namely a stylet actuator 16 and an anchoring actuator 18. Stylet actuator 16 is coupled to a follower 20 which is rigidly secured to a follower arm 21. Anchoring actuator 18 is used to drive anchors 80 into the tissue to anchor the operative end of the device in a position and in a manner described in the above referenced patent publication.

Stylet actuator 16 and anchoring actuator 18 are supported within handle portion 14. Handle portion 14 comprises a left handle housing half 28 and a right housing half which is symmetrical in shape to and a mirror image of left housing half 28, but not illustrated.

As illustrated in FIGS. 1-4, the inventive ablation instrument may be configured in the deployed state. Alternatively, as illustrated in FIG. 5, the inventive ablation instrument 10 may be configured with either the anchors and/or the ablation stylets in an undeployed state.

Figure 4:
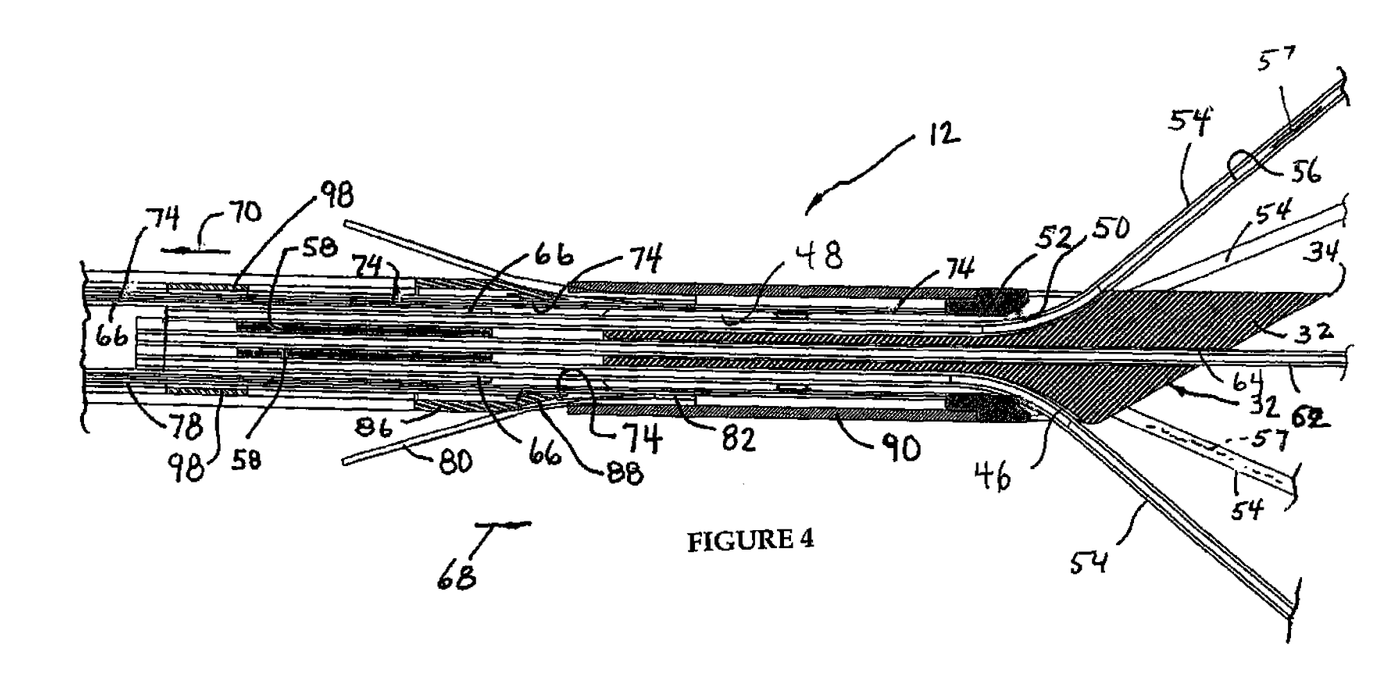
FIG. 4 is a cross-sectional view illustrating deployed hypotubes and anchors.
Figure 5:
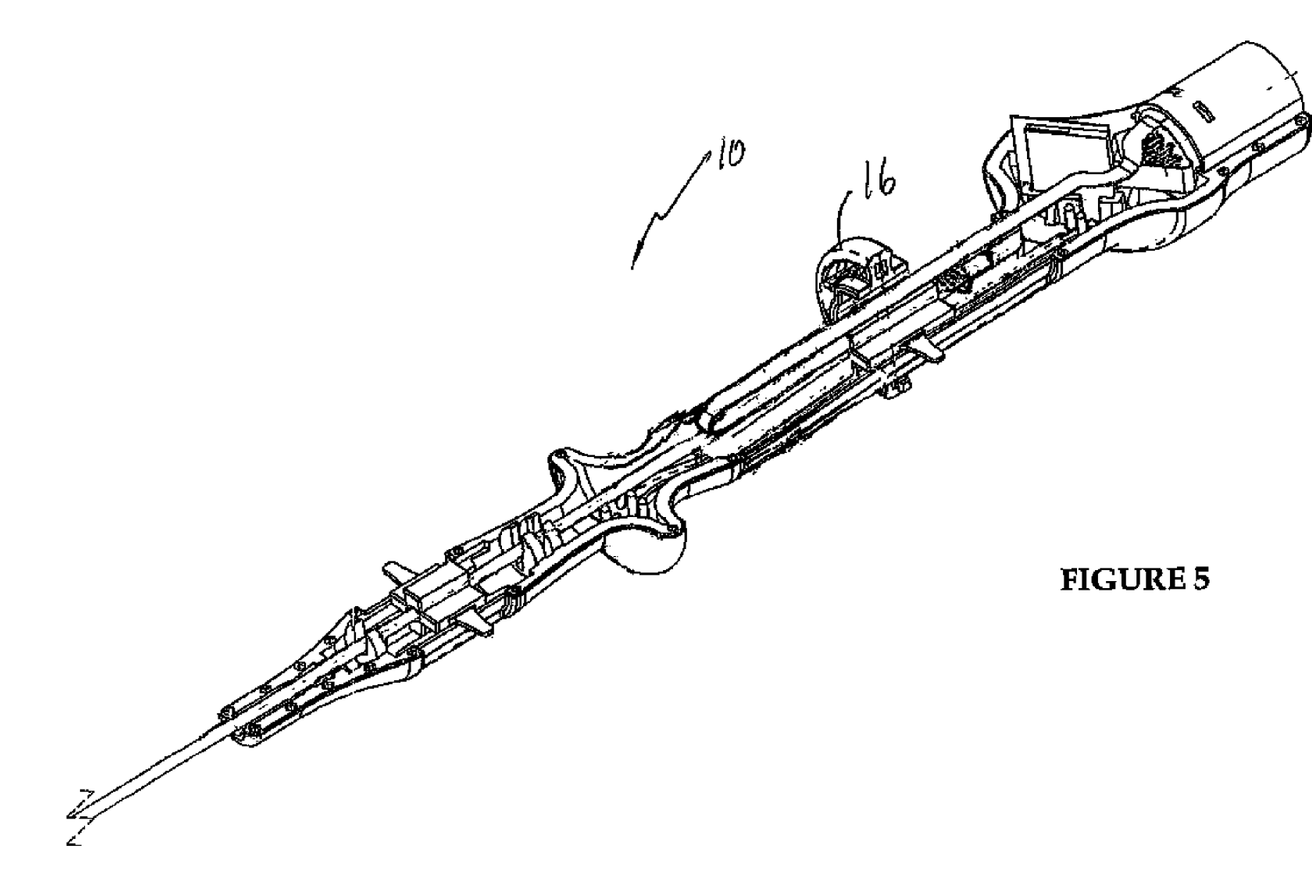
FIG. 5 is a perspective view similar to FIG. 1 with the stylet actuator in a position to put the stylets in the retracted position.

Generally, any example, the ablation mechanism works by providing plurality of deflection surfaces 46 which are positioned at the end of longitudinal grooves 48, as illustrated in FIG. 4. These surfaces 46 are configured to gently bend the flexible hypotube stylets 54 (which are excited with radiofrequency energy during the ablation of uterine fibroid tissue), causing them to exit catheter 12 and follow substantially straight paths through the tissue to be ablated. During this deflection, the action of deflection surfaces 46 is complemented by the inside curved surface 50 of insulative Teflon deflector ring 52.

The deflection of a plurality of hypotubes 54 is illustrated in FIG. 4. Hypotubes 54 are flexible hollow tubes made of steel or nickel titanium alloy. Hypotubes 54, as well as, all other steel parts of the inventive ablation device 10, are preferably, for economic and/or performance reasons, made of stainless steel or other high quality steel, except as indicated herein. The tubes define an internal volume 56 which contains a wire thermocouple 57, which performs the function of measuring the temperature of the ablated tissue which, over time, allows control of the ablation operation and ensures that the ablated tissue will become necrotic. In FIG. 4, the thermocouples 57 are shown in only one of the tubes for purposes of clarity of illustration.

Figures 6, 7, 8:
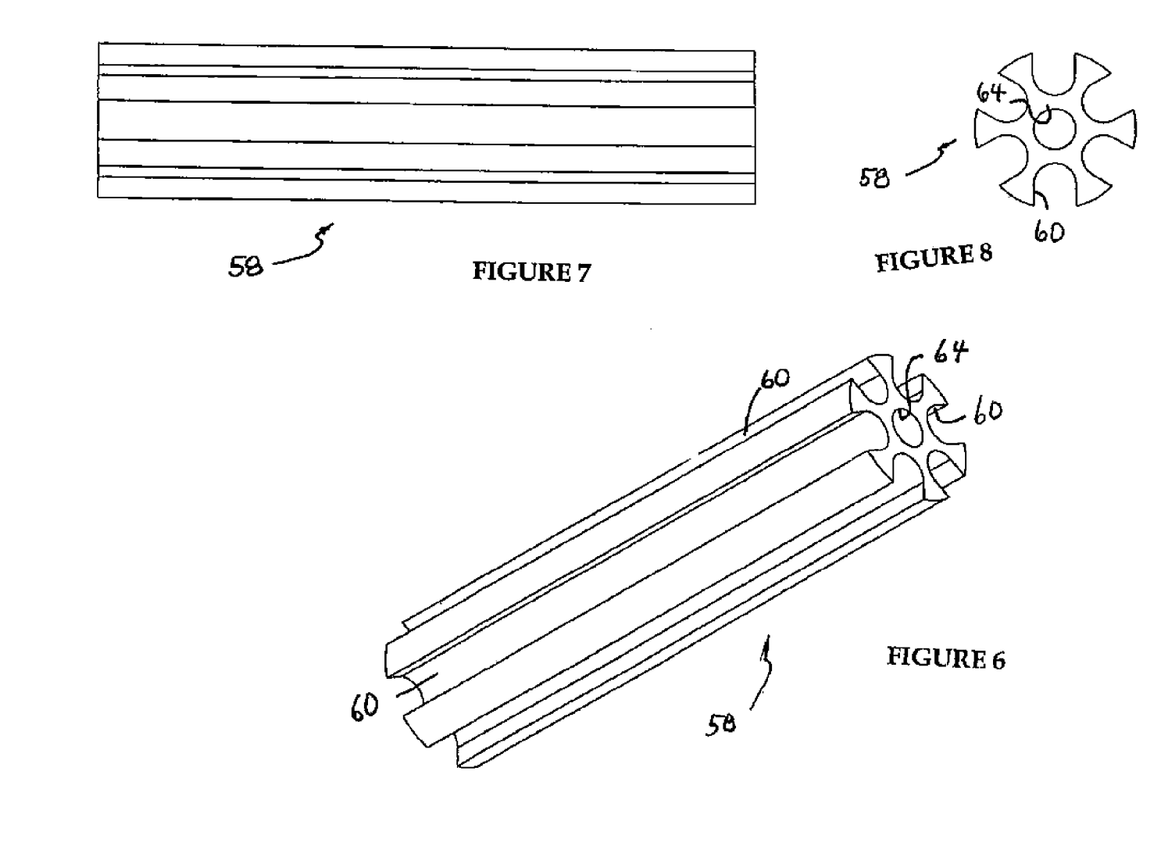
FIG. 6 is a perspective view illustrating a core for holding a plurality of hypotubes.
FIG. 7 is a side plan view illustrating a core for holding a plurality of hypotubes.
FIG. 8 is a rear view illustrating the core of FIG. 6 for holding a plurality of hypotubes.
Figure 9:
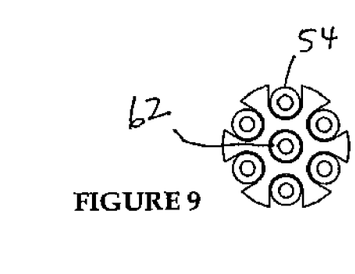
FIG. 9 is a rear view illustrating the core of FIG. 6 for holding a plurality of hypotubes.
Figure 10:
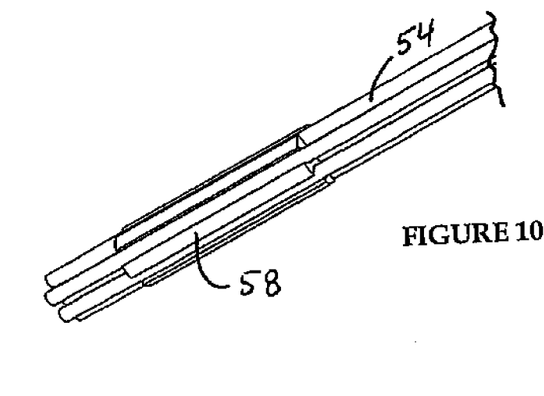
FIG. 10 is a perspective detailed view illustrating a core holding a plurality of hypotubes.
Figure 11:
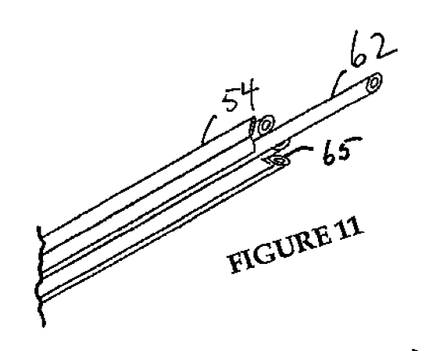
FIG. 11 is a perspective detailed view illustrating the tips of a plurality of hypotubes when they are being held in a core as illustrated in FIG. 19.
Figure 12:
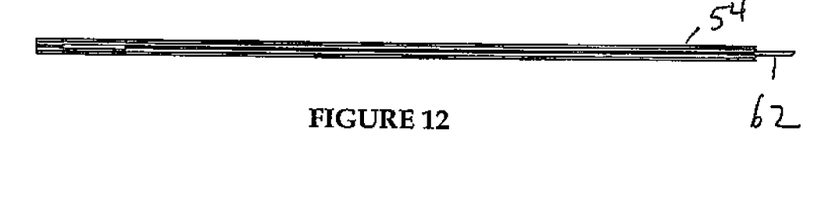
FIG. 12 is a side plan view illustrating the core and stylets.

Hypotubes 54 slidably move in longitudinal grooves 48. Hypotubes 54, which function as ablation electrodes, are mounted on a needle core 58, illustrated in FIGS. 6-8. Needle core 58 includes a plurality of longitudinal grooves 60. Each of six hypotube stylets 54 is mounted in its respective longitudinal groove 60 and secured in groove 60 by friction or through the use of an adhesive. Alternatively, a wraparound tubular shrink plastic member may be used to secure them in position. A seventh hypotube 62 is mounted in a central axial bore 64. The assembly of hypotubes 54 and 62 in needle core 58 is illustrated in FIGS. 9-11. The mounting of hypotubes 54 in needle core 58 is illustrated most clearly in perspective in FIG. 12.

Referring to FIG. 4, a flexible steel electrode push tube 66 is disposed around and secured to needle core 58 with the needles mounted in it. Sliding movement of the hypotubes 54 in longitudinal grooves 48 is achieved by movement of electrode push tube 66. Movement in direction 68 causes the deployment of hypotubes 54 and 62. Movement in direction 70 causes retraction of the hypotubes.

Referring to FIGS. 2 and 3, a flexible steel electrode mandrel tube 74 is disposed around and over electrode push tube 66. Flexible steel electrode mandrel tube 74 allows electrode push tube 66 to freely slide within it. This is achieved, despite the relatively large area of the tubes, because the facing surfaces of the tubes are both smooth and because there is a small gap between their facing surfaces, thus minimizing friction. Such gaps allow provision for flushing the instrument clean with water, as is done with prior art devices. A flexible plastic tubular insulative member 76 is disposed around and over electrode mandrel tube 74.

Insulative member 76 isolates electrical radiofrequency ablation energy (carried by push tube 66 for exciting hypotubes 54 and 62) from anchor push tube 78. This allows electrical ablation energy to be optionally applied to anchor push tube 78 to independently cause the anchors 80 on anchor member 82 to apply ablation energy to a different volume than that which is ablated by the electrode stylets 54 and 62.

The structure of the distal end of catheter portion 12 is completed by a steel anchor cover 90, which is supported on, surrounds and is secured to insulating ring 52. During deflection, anchors 80 pass between deflection surfaces 88 and the inside surface of steel anchor cover 90.

The structure of catheter 12 is completed by outer tube 96 which is secured to the handle formed by the two handle halves 14 at one end and secured to a tubular slip ring 98 which slides over anchor push tube 78.

Electrode mandrel tube 74 is secured at its proximal end to handle 14. At its distal end, electrode mandrel tube 74 is secured to trocar 32. Alternately, instead of or in addition to using an adhesive, electrode mandrel tube 74 may be crimped. Stylet actuator 16 is secured to electrode push tube 66. Thus, movement in the direction of arrow 68 in FIG. 4 causes the stylets to emerge from the end of the catheter as illustrated in FIGS. 2 and 4. Full deployment of ablation electrodes or stylets 54 and 62 is illustrated most clearly in FIGS. 2 and 3.

As shown in FIG. 1, anchoring actuator 18 is secured to anchor push tube 78 at its proximal end. At its distal end, electrode mandrel tube 74 is secured to anchor mandrel 86, for example by a quantity of epoxy adhesive. Accordingly, movement of anchoring actuator 18, in the direction of arrow 70 in FIG. 4, causes the anchors 80 to emerge from the catheter as illustrated in FIGS. 2-4.

Referring to FIG. 1, it can be seen that a flexible coupling conductor made of plastic, for example mylar, can define a printed circuit member 51 that is provided for coupling thermocouple leads 57. Only one such thermocouple lead is illustrated for purposes of clarity of illustration, but it is to be understood that each of the stylets 54 and 62 has its own respective thermocouple leads and that all of the thermocouple leads 57 exit electrode push tube 66. At the point of exit, the quantity of epoxy may be used to secure them in position to the outside of the electrode push tube 66.

The structure of flexible circuit 51 may be seen most clearly with reference to FIGS. 13-16. Flexible circuit 51 includes a plurality of printed circuit conductors 53 which extend between soldering holes 55 at their distal ends. There are a plurality, for example seven, printed circuit conductors 53, corresponding to the six thermocouple leads 57 and a seventh to provide RF energy to their associated six ablation stylets 54 and 62. Holes 55 are surrounded by conductive material in electrical contact with the leads 53, as is typically done in the printed circuit art. Holes 55 are electrically connected to thermocouple leads 57 by soldering to thermocouple leads 57. The seventh of lead is connected to hole 59, which is adapted to snugly fit around and allow electrical coupling to electrode push tube 66.

Figures 13, 15:
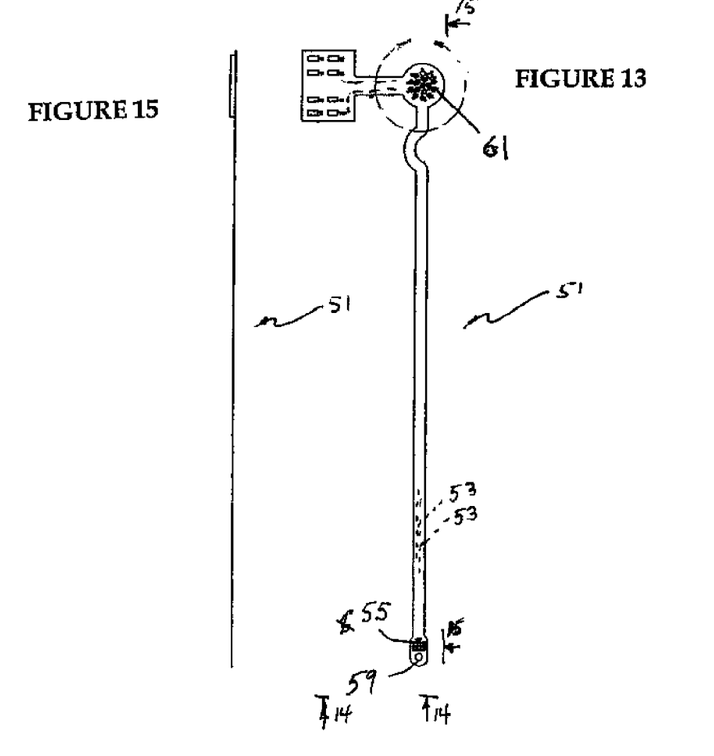
FIG. 13 is a plan view illustrating the flexible circuit used in accordance with the present invention.
FIG. 15 is a view along the lines 15-15 of FIG. 13.
Figure 14:
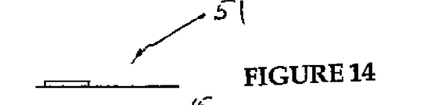
FIG. 14 is a view along the lines 14-14 of FIG. 13.
Figure 16:
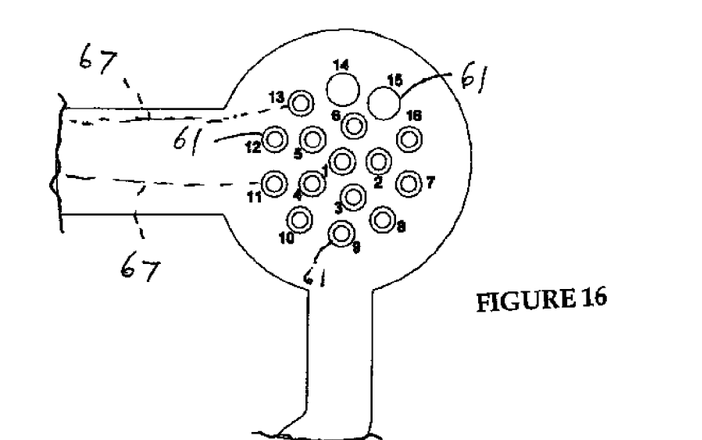
FIG. 16 an enlarged view of the area indicated in dashed lines in FIG. 13.

Referring now to FIG. 13, the other ends of the leads 53, which are connected to holes 61, allow connection to connector 63 (connector 63 is shown in FIG. 1). Such connection is achieved by welding to connector pins 65.

As alluded to above, RF energy is applied to the lead associated with the hole 59 by the connection through connector 63 to the pin 65 which carries RF energy from the console. This is achieved by folding the flexible circuit 51 from the position illustrated in FIGS. 13 to 15 to the position illustrated in FIG. 5, and soldering electrode push tube 66 to that portion of the printed circuit surrounding hole 59.

Also as alluded to above, pins 65 are coupled to respective leads 53 in order to carry data from file thermocouples respecting the temperature of tissue surrounding each of their respective ablation stylets. Finally, flexible circuit 51 includes leads 67 which couple holes 61 to soldering pins 65 that are not coupled to the leads coupled to the thermocouple leads.

Figure 17:
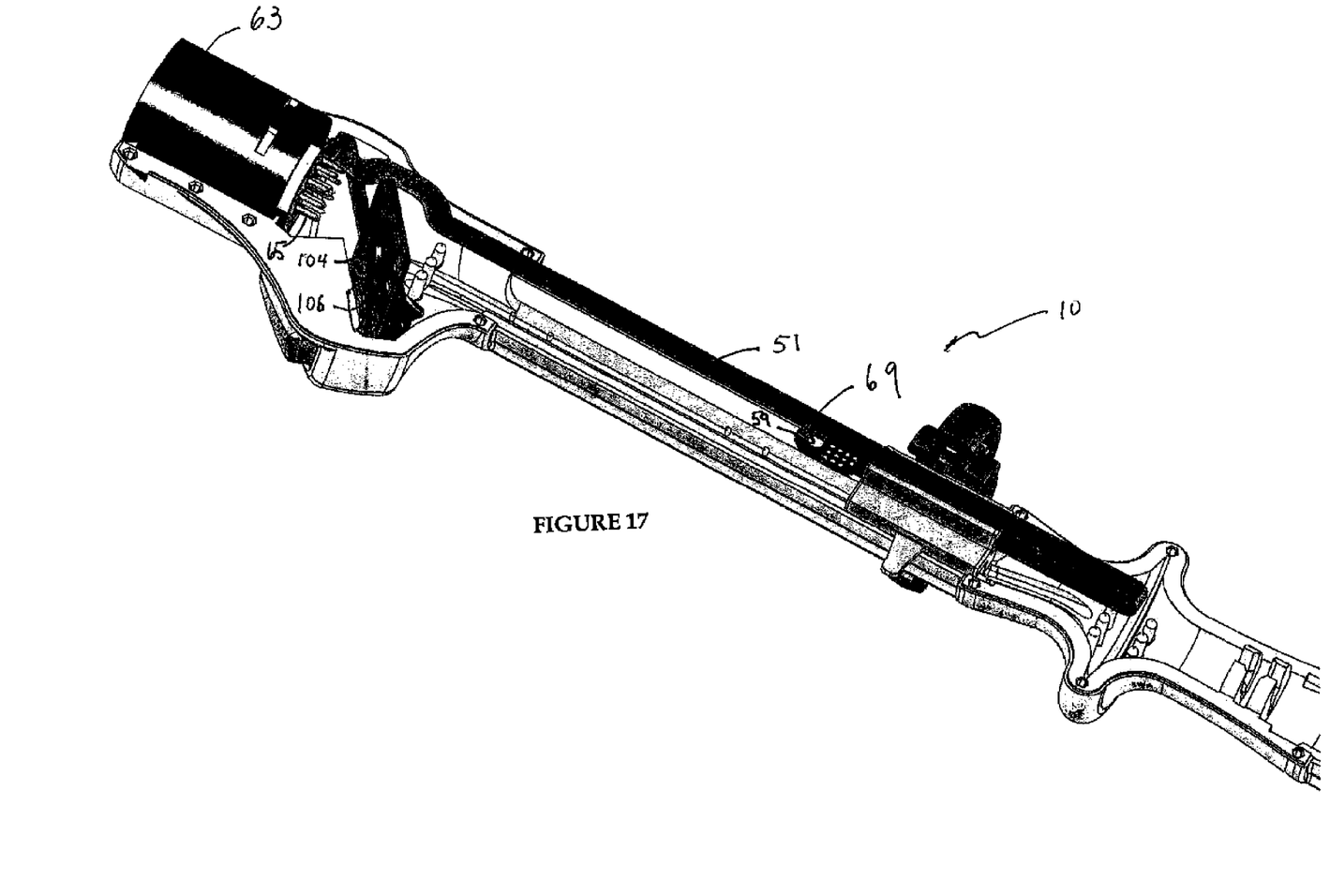
FIG. 17 is a perspective view of the inventive instrument from a different perspective as compared to FIG. 1.
Figure 18:
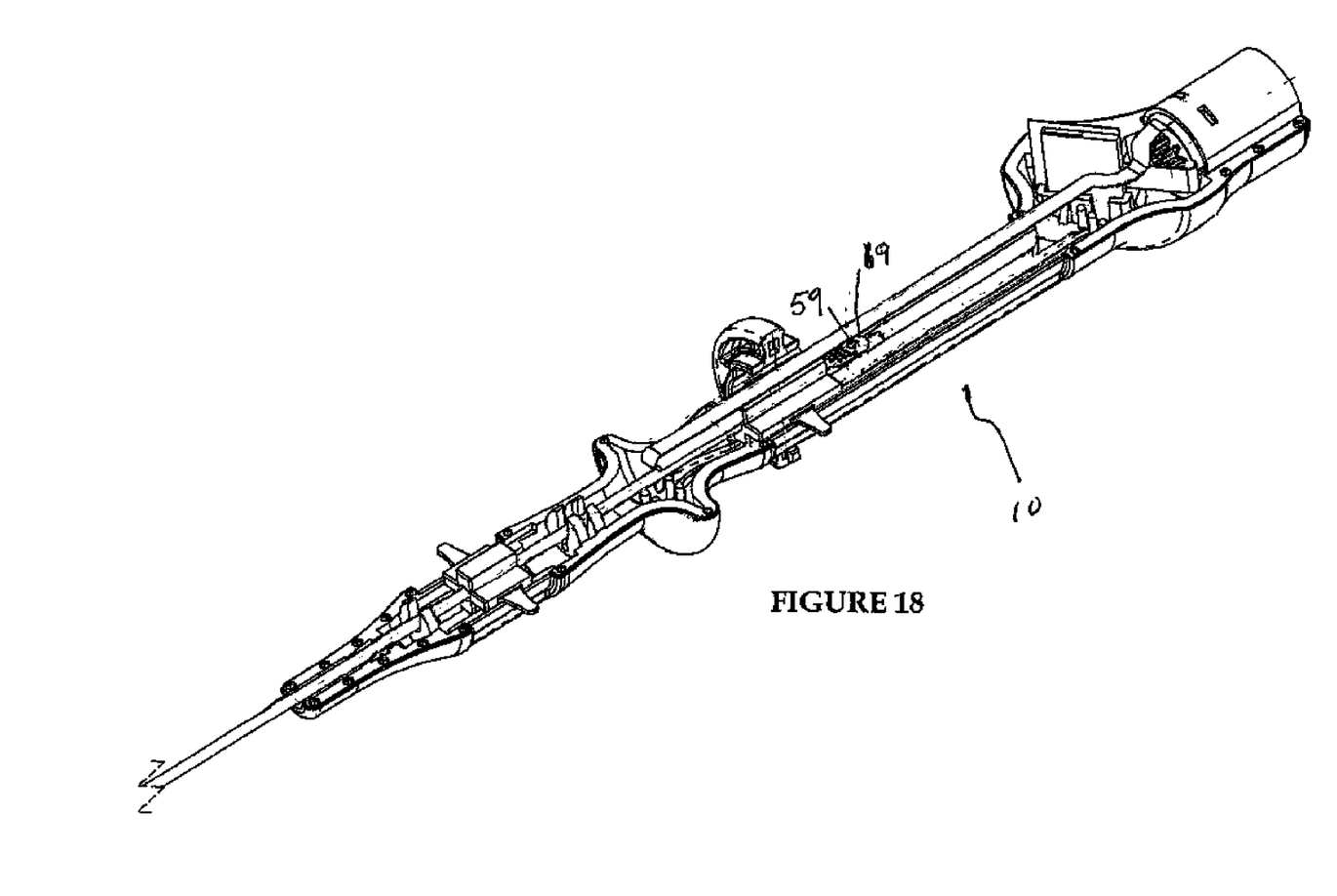
FIG. 18 is a view similar to FIG. 1 showing the placement of the flexible circuit prior to its being disposed around the tube which actuates the stylets.

In accordance with the present invention, it is contemplated that control of the inventive ablation device 10 will be achieved by one or two electrical switches 104 and 106 as illustrated in FIG. 17. Operation of switch 106 may cause the appearance of a menu on a display. Repeated suppressing of switch 104 may be designed to effect navigation through a menu to switch between different menu items, such as controlling ablation time, controlling ablation temperature, or some other parameter. When the desired value is seen on the screen by the surgeon, selective actuation of the switch may be programmed to register that value with the electronic circuit controlling ablation. In such event, this will cause the inventive ablation device 10 to be operated in accordance with the selected parameter.

RF ablation energy, control signals, and temperature measurement signals are coupled from the inventive ablation device 10 to a control unit/RF energy source by a connector 63. In accordance with the present invention, it is contemplated that a conventional radiofrequency energy source such as that used in conventional ablation systems would be employed in conjunction with the inventive ablation device 10.

When it is desired to use the inventive ablation instrument 10, stylet actuator 16 may be advanced from the position illustrated in FIG. 5 to the position illustrated in FIG. 1. During such movement, flexible electrode 51 remains folded but as movement occurs the position of the fold changes, thus resulting in a different effective length at that point between the end of electrode push tube 66 and connector 63. Through this movement, an effective electrical connection is achieved without the possibility of jamming or other effects which may compromise the ability of the surgeon to operate instrument 10 during an operation.

The result is to advance the stylets which wholly are contained within trocar 32 to the positions illustrated, for example, in FIG. 4. Once the stylets are positioned within the tissue to be ablated, energy may be applied thereto. At the same time the temperature of the tissue surrounding a stylet may be measured, with the objective of reducing or wholly eliminating the application of RF ablation energy when the temperature becomes so high that charring of the tissue is possible, which would make continued ablation impossible or impractical without withdrawing the stylets into the trocar and repositioning the trocar and redeploying the stylets in new positions.

While the inventive device has been illustrated for use in the ablation of uterine fibroids, it is understood that this particular implementation is exemplary and that the inventive device may be employed in a wide variety of circumstances. Likewise, while an illustrative embodiment of the invention has been described, it is understood that various modifications to the structure of the disclosed device will be obvious to those of ordinary skill in the art. Such modifications are within the spirit and scope of the invention which is limited and defined only by the appended claims.

The invention claimed is:

1. An ablation instrument, comprising:
   (a) an elongated cannula having a proximal end and a distal end, said cannula defining an internal lumen within said cannula and a cannula axis;
   (b) an elongated flat flexible, moveable member having a proximal end and a distal end, said elongated flexible, moveable member having a thickness, a length and a width, and being configured to have a first portion that is substantially straight, a second portion configured in a curved configuration and a third portion configured to be substantially straight, said second portion being positioned between said first and third portions, said first and third portions being positioned in facing spaced relationship to each other, said first and third portions extending substantially in the direction of the cannula axis, at least one of said first and third portions extending in the direction of the cannula axis with a length substantially longer than its width;
   (c) a printed circuit power coupling conductor disposed on said elongated flat flexible, moveable member and extending along the length of said elongated flat flexible movable member, said printed circuit power coupling conductor having a proximal end and a distal end,
   d) an RF source, said proximal end of said printed circuit power coupling conductor coupled to receive RF ablation energy from said RF source;
   (e) a plurality of flexible signal coupling conductors disposed along the length of said elongated flat flexible member;
   (f) a plurality of temperature measurement signal conductors contained within said lumen, each of said conductors having a proximal end, and a distal end, said proximal ends of said temperature measurement signal conductors being coupled to the distal ends of said flexible signal coupling conductors;

(g) a plurality of temperature sensing transducers, each coupled to a respective one of said distal ends of said temperature measurement signal conductors;

(h) an RF ablation energy conductor having a proximal end proximate the proximal end of said cannula and a distal end proximate the distal end of said cannula, said proximal end of said RF ablation energy conductor being coupled to a distal end of said printed circuit power coupling conductor;

(i) a plurality of ablation stylets each having a proximal end and a distal end, and each coupled at the respective proximal end of said stylet to the distal end of said RF ablation energy conductor, said stylets comprising a deflectable material, said RF ablation energy conductor together with said stylets being mounted for axial movement;

(j) a head defined proximate the distal end of said cannula; and (k) a deflection surface positioned proximate said head, the deflection surface being configured and positioned to deflect, in response to axial movement of said stylets in a direction from said proximate end of said cannula to said distal end of said cannula, at least some of said stylets laterally with respect to said cannula axis in different directions along substantially straight paths, said paths defining an ablation volume.

2. An ablation instrument as in claim 1, wherein said elongated flat flexible, moveable member comprises an arm portion, and further comprising a second plurality of flexible conductors disposed on said arm portion, and an electrical switching device disposed on said arm portion and coupled to said second plurality of conductors.

3. An ablation instrument as in claim 1, wherein said plurality of flexible signal coupling conductors disposed along the length of said elongated flat flexible, moveable member has proximal ends electrically connected to an electrical connector.

4. An ablation instrument as in claim 3, wherein said elongated flat flexible, moveable member comprises an arm portion, and further comprising a second plurality of flexible conductors disposed on said arm portion, and an electrical switching device disposed on said arm portion and coupled to said second plurality of conductors.

5. An ablation instrument as in claim 1, wherein said head is a trocar point.

6. An ablation instrument as in claim 1, wherein said head has a rounded configuration.

7. An ablation instrument as in claim 1, wherein each of said stylets are configured to assume a substantially straight configuration in the absence of external forces.

8. An ablation instrument as in claim 1, wherein said plurality of conductors are secured at a point proximate said proximal end of said elongated flat flexible, moveable member.

* * * * *